(12) United States Patent
Nebolsin et al.

(10) Patent No.: US 9,351,960 B2
(45) Date of Patent: May 31, 2016

(54) AGENT FOR THE TREATMENT OF VIRAL HEPATITIS C

(71) Applicant: OBSSCHESTVO S OGRANICHENNOI OTVETSTVENNOSTIYU "PHARMENTERPRISES", Moscow (RU)

(72) Inventors: Vladimir Evgenievich Nebolsin, Moscow (RU); Dmitry Yurievich Konstantinov, Samara (RU); Larisa Leonidovna Popova, Samara (RU); Elena Alekseevna Strebkova, Samara (RU); Petr Grigorievich Deryabin, Moscow (RU)

(73) Assignee: OBSCHESTVO S OGRANICHENNOI OTVETSTVENNOSTIYU "PHARMENTERPRISES", Moscow (RU)

( * ) Notice: Subject to any disclaimer, the term of this patent is extended or adjusted under 35 U.S.C. 154(b) by 0 days.

(21) Appl. No.: 14/384,737

(22) PCT Filed: Mar. 13, 2013

(86) PCT No.: PCT/RU2013/000193
§ 371 (c)(1),
(2) Date: Sep. 12, 2014

(87) PCT Pub. No.: WO2013/137782
PCT Pub. Date: Sep. 19, 2013

(65) Prior Publication Data
US 2015/0064135 A1    Mar. 5, 2015

(30) Foreign Application Priority Data

Mar. 14, 2012  (RU) ................................ 2012109938

(51) Int. Cl.
| | | |
|---|---|---|
| *A61K 31/417* | (2006.01) | |
| *A61K 38/05* | (2006.01) | |
| *A61K 38/21* | (2006.01) | |
| *A61K 31/7056* | (2006.01) | |

(52) U.S. Cl.
CPC ........... *A61K 31/417* (2013.01); *A61K 31/7056* (2013.01); *A61K 38/05* (2013.01); *A61K 38/21* (2013.01); *A61K 38/212* (2013.01)

(58) Field of Classification Search
None
See application file for complete search history.

(56) References Cited

U.S. PATENT DOCUMENTS

2012/0129908 A1*  5/2012  Nebolsin et al. ............... 514/400

* cited by examiner

*Primary Examiner* — Thomas S Heard
(74) *Attorney, Agent, or Firm* — Banner & Witcoff, Ltd.

(57) ABSTRACT

The invention relates to medicine and comprises an agent for the treatment of a viral hepatitis C, which is glutaryl histamine or a pharmaceutically acceptable salt thereof. This agent can also be administered in combination with a pegylated interferon and ribavirin. The invention further relates to a pharmaceutical composition for the treatment of a viral hepatitis C. This invention solves the problem of providing a novel agent, which is effective in the treatment of a viral hepatitis C and makes it possible to produce a sustained virologic response.

27 Claims, No Drawings

AGENT FOR THE TREATMENT OF VIRAL HEPATITIS C

CROSS-REFERENCE TO RELATED APPLICATIONS

This application is a U.S. National Stage application under 35 U.S.C. §371 of International Application PCT/RU2013/000193 (published as WO 2013/137782 A1), filed Mar. 13, 2013, which claims priority to Application RU 2012109938, filed Mar. 14, 2012. Benefit of the filing date of each of these prior applications is hereby claimed. Each of these prior applications is hereby incorporated by reference in its entirety.

FIELD OF THE INVENTION

The present invention relates to the field of medicine, in particular to the use of glutaryl histamine or a pharmaceutically acceptable salt thereof for the treatment of viral hepatitis C.

BACKGROUND

Viral hepatitis C remains one of the most actual problems of the healthcare in the world. A large quantity of infected persons (almost 200 million persons), a high risk of developing chronic infection (60-80%) which results in hepatic cirrhosis or hepatocellular carcinoma (15-25%), the development of systemic extrahepatic lesions of human organs and tissues, and the lack of a vaccine for the prevention of the development and spread of the infection are the reasons for the development of effective treatment of hepatitis C [Abdurakhmanov D. T. Prospects of the treatment of chronic hepatitis C.//The Clinical Hepatology, 2010; 3:3-11]

Modern therapy of hepatitis C with pegylated interferon α2a or α2b in combination with ribavirin makes it possible to produce a sustained virologic response (SVR) in 54-73% of cases. [Ivashkin V. T., Lobsin Ju. V, Storozhakov G. I. et al]. Efficiency and safety of 48-week therapy with pegylated interferon α2a and ribavirin was demonstrated for newly-admitted patients with chronic hepatitis C [Clin. Pharm. Ther., 2007, 16(1), 1-5]. In case of infection with hepatitis C virus (HCV) subtype 1b, which prevails in Russia, the percentage of effective therapy significantly decreases and is of 40-50%.

Thus, there is a need for the development of more effective, affordable, and economically viable agents and schemes of the treatment of hepatitis C, which have fewer side effects.

The present inventors have unexpectedly found that glutaryl histamine can be used for the treatment of hepatitis C. With that, glutaryl histamine has an antiviral effect against hepatitis C virus, used both alone and in combination with pegylated interferon and ribavirin.

Previously, glutaryl histamine was not supposed to be used for the treatment of viral hepatitis. Furthermore, a combination of glutaryl histamine with pegylated interferon and ribavirin previously was not known.

Thus, the objective of the present invention is to provide new agent for the treatment of hepatitis C, and a combination of medicaments that have an enhanced efficiency in the treatment of viral hepatitis C in comparison with the most effective combination of medicaments used before the present invention.

SUMMARY OF THE INVENTION

The above objective is addressed by the subject matters of the present invention characterized in the claims.

The present invention relates to a field of medicine and includes an agent for the treatment of viral hepatitis C comprising glutaryl histamine or a pharmaceutically acceptable salt thereof.

The invention also includes an agent for producing a sustained virologic response in the treatment of viral hepatitis C, the agent comprising glutaryl histamine or a pharmaceutically acceptable salt thereof.

In a preferable embodiment of the invention, glutaryl histamine is comprised in Dicarbamine preparation. The dose of glutaryl histamine or a pharmaceutically acceptable salt thereof is from 0.1 to 10 mg/kg of body weight. A single dose of the glutaryl histamine can be 100 mg. Duration of the administration of glutaryl histamine may be from 3 weeks to 12 months. The course of viral hepatitis C therapy provides a decrease in side effects of antiviral therapy such as influenza-like syndrome, arthralgia, myalgia, exacerbation of chronic pancreatitis, depression, loss of hair, leucopenia or neutropenia.

The agent for the treatment of viral hepatitis C, which is glutaryl histamine or a pharmaceutically acceptable salt thereof, can also be used together with an effective amount of pegylated interferon and ribavirin.

The invention also relates to an agent for producing a sustained virologic response in the treatment of viral hepatitis C, comprising glutaryl histamine or a pharmaceutically acceptable salt thereof.

Glutaryl histamine has the following structural formula:

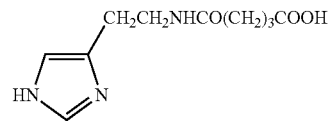

Furthermore, the invention relates to a pharmaceutical composition for the treatment of hepatitis C, comprising an effective amount of glutaryl histamine or a pharmaceutically acceptable salt thereof. The effective amount of the glutaryl histamine or the pharmaceutically acceptable salt thereof may be of from 0.1 to 10 mg/kg of body weight.

The invention also includes a pharmaceutical combination for the treatment of hepatitis C, comprising pegylated interferon, ribavirin, and glutaryl histamine or a pharmaceutically acceptable salt thereof.

Further, the invention relates to a kit for the treatment of hepatitis C, comprising pegylated interferon, ribavirin, glutaryl histamine or a pharmaceutically acceptable salt thereof, and the instructions for use.

The invention also relates to the use of glutaryl histamine or a pharmaceutically acceptable salt thereof for the manufacture of a pharmaceutical composition for the treatment of viral hepatitis C.

In addition, the invention includes use of glutaryl histamine or a pharmaceutically acceptable salt thereof in combination with pegylated interferon and ribavirin for the treatment of hepatitis C.

The viral hepatitis C to be treated in accordance with the invention may be acute or chronic hepatitis C.

The agent for the treatment of hepatitis C according to the invention provides a decrease in side effects of antiviral therapy. These said effects of antiviral therapy may be influenza-like syndrome, arthralgia, myalgia, exacerbation of chronic pancreatitis, depression, and/or loss of hair.

Preferably, glutaryl histamine is administered as a constituent of Dicarbamine preparation. The dose of glutaryl histamine or a pharmaceutically acceptable salt thereof is from 0.1 to 10 mg/kg of body weight.

The pegylated interferon used in combination with glutaryl histamine and ribavirin may be pegylated interferon α2a or pegylated interferon α2b.

In a preferable embodiment of the invention the dose of glutaryl histamine is of 100 mg when administered once daily; the dose of pegylated interferon is of 100 μg or 1.5 μg/kg when administered once weekly; and the dose of ribavirin is of 1000 mg per day in daily administration.

Duration of the administration of glutaryl histamine preferably is from 3 weeks to 12 months.

Glutaryl histamine can be used in the form of pharmaceutically acceptable salts produced by reacting, for example, with sodium hydroxide, potassium hydroxide, magnesium carbonate, lithium hydroxide, or calcium carbonate by routine methods widely described in the literature.

The invention also relates to a method for treating hepatitis C, comprising administering to a patient an effective amount of glutaryl histamine or a pharmaceutically acceptable salt thereof.

The invention further includes a method for treating viral hepatitis C, comprising administering to a patient an effective amount of pegylated interferon, ribavirin and glutaryl histamine or a pharmaceutically acceptable salt thereof.

In addition, the invention relates to a method for achieving a sustained virologic response in the treatment of viral hepatitis C, comprising administering to a patient an effective amount of pegylated interferon, ribavirin and glutaryl histamine or a pharmaceutically acceptable salt thereof.

Positive effects achieved by carrying out the invention are as follows. Unexpectedly, a new drug to treat hepatitis C has been found that has a pronounced antiviral effect. In addition, a powerful combination of drugs for the treatment of viral hepatitis C has been developed. Also surprisingly, significant improvements have been achieved in the most important parameters of the efficacy of antiviral therapy, such as a rapid virologic response (absence of HCV RNA in serum when studied with a sensitive test system 4 weeks after the treatment initiation), an early virologic response (absence of HCV RNA in serum when studied with a sensitive test system 12 weeks after the treatment initiation), an immediate virologic response (absence of HCV RNA in serum when studied with a sensitive test system 24 and 48 weeks after the treatment initiation) and a sustained virologic response in patients with chronic hepatitis C (absence of HCV RNA in serum when studied with sensitive test system 24 weeks after the treatment completion).

In addition, HCV treatment according to the invention has demonstrated a significant reduction in the incidence of side effects of antiviral therapy, such as leukopenia, neutropenia, influenza-like syndrome, arthralgia, myalgia, exacerbation of chronic pancreatitis, depression, and hair loss.

EMBODIMENTS OF THE INVENTION

Hitherto an insurmountable difficulty was to conduct drug screening on experimental models of infection caused by the hepatitis C virus.

For this purpose, there has been developed an experimental model of an in vitro hepatitis C virus infection of cultures of primary and continuous cells, which are susceptible to HCV replication. As a result, there were isolated and identified cytopathogenic HCV variants belonging to different genotypes, including genotype 1b, which is the most widespread in Russia, the most pathogenic, and which infections are difficult to treat with interferon. Acute and chronic hepatitis C virus infections of cell cultures of different origin have been reproduced. Thus, in regard to hepatitis C, a unique opportunity has emerged not only for screening compounds, but also for preclinical assessment of antiviral activity of preparations.

EXAMPLE 1

The study was aimed to determine antiviral activity of glutaryl histamine in an experimental model of hepatitis C virus infection of cell cultures.

The study was conducted in a cytopathogenic hepatitis C virus (HCV) strain of genotype 1b. The strain was isolated from the serum of a patient with chronic hepatitis C, and identified as a hepatitis C virus. Infectious HCV doses used were equal to 10.0 tissue cytopathogenic doses ($TCID_{50}$)/20 μL.

The used primary fibroblasts highly sensitive to cytopathogenic action of HCV were obtained after trypsinization of 9-day-old chick embryos (FEC), and the used pig embryonic kidney cell (SPEV) cultures were obtained from the Collection of Cell Cultures of the Institute of Virology RAMS. They were used in the form of a one-day cell monolayer grown in 24-well plastic plates. The SPEV and FEC cell cultures were cultured in medium 199 with 10% fetal calf serum, supplemented with glutamine and antibiotics (100 U/ml).

A glutaryl histamine solution used in the study was prepared on the basis of the culture medium used for culturing infected cell cultures. To study the antiviral activity of the drug, a 50 μL of a solution thereof taken in various dilutions were added to the FEC cultures at the time of infection, 24 hours before and 24 hours after infection of the cells.

The infectious activity of HCV was assessed according to the results of titration of fluid samples in the SPEV cell cultures, wherein the culture fluids were derived from the HCV-infected FEC or SPEV cultures on 2 and 5 days after infection. The results were usually registered 6 or 7 days after infection, when the viral cytopathic effect reached its maximum, using the Reed and Muench formula to determine HCV titers.

The obtained results are shown in Tables 1-4.

TABLE 1

Antiviral activity of glutaryl histamine in a model of FEC cell cultures infected with HCV. Samples were accessed on Day 2 after infection and treatment of the cells with the drug

| Time of treatment with glutaryl histamine | HCV titers (lg $TCID_{50}$ for SPEV cell cultures) in medium samples derived from FEC cultures on Day 2 after infection and treatment of the cells with the drug at concentrations of (μg/mL): 500.0 | 50.0 | 5.0 | 0.5 | 0.05 | 0.005 | Virus control |
|---|---|---|---|---|---|---|---|
| At the time of infection | 5.5 | 6.2 | 6.5 | 6.0 | 5.0 | 5.5 | 6.5 |
| 24 hours before infection | 4.5 | 4.5 | 4.5 | 4.5 | 4.5 | 5.0 | 6.5 |
| 24 hours after infection | 0 | 2.5 | 0 | 0 | 1.8 | 0 | 6.5 |

TABLE 2

Antiviral activity of glutaryl histamine in a model of pig embryonic kidney cell (SPEV) cultures infected with HCV. Samples were accessed on Day 3 after infection and treatment of the cells with the drug

| Time of treatment | HCV titers (lg $TCID_{50}$ for SPEV cell cultures) in medium samples treated on Day 3 after infection and treatment with glutaryl histamine at concentrations of (µg/mL): | | | | | | |
|---|---|---|---|---|---|---|---|
| with glutaryl histamine | 500.0 | 50.0 | 5.0 | 0.5 | 0.05 | 0.005 | Virus control |
| At the time of infection | 3.0 | 3.5 | 2.3 | 3.3 | 3.3 | 3.3 | 3.3 |
| 24 hours before infection | 3.5 | 3.5 | 3.5 | 3.2 | 3.2 | 3.0 | 3.3 |
| 24 hours after infection | 0 | 1.25 | 0 | 0 | <1.0 | 0 | 3.3 |

TABLE 3

Antiviral activity of glutaryl histamine in a model of pig embryonic kidney cell (SPEV) cultures infected with HCV. Samples were accessed on Day 4 after infection and treatment of the cells with the drug

| Time of treatment | HCV titers (lg $TCID_{50}$ for SPEV cell cultures) in medium samples treated on Day 4 after infection and treatment with glutaryl histamine at concentrations of (µg/mL): | | | | | | |
|---|---|---|---|---|---|---|---|
| with glutaryl histamine | 500.0 | 50.0 | 5.0 | 0.5 | 0.05 | 0.005 | Virus control |
| At the time infection | 4.2 | 5.0 | 5.5 | 4.1 | 4.4 | 4.1 | 4.6 |
| 24 hours before infection | 3.8 | 3.8 | 3.4 | 3.8 | 3.0 | 3.4 | 4.6 |
| 24 hours after infection | 0 | 2.6 | 0 | 0 | 1.3 | 0 | 4.6 |

TABLE 4

Antiviral activity of glutaryl histamine in a model of pig embryonic kidney cell (SPEV) cultures infected with HCV. Samples were accessed on Day 5 after infection and treatment of the cells with the drug

| Time of treatment | HCV titers (lg $TCID_{50}$ for SPEV cell cultures) in medium samples treated on Day 5 after infection and treatment with glutaryl histamine at concentrations of (µg/mL): | | | | | | |
|---|---|---|---|---|---|---|---|
| with glutaryl histamine | 500.0 | 50.0 | 5.0 | 0.5 | 0.05 | 0.005 | Virus control |
| At the time of infection | 5.5 | 7.0 | 5.5 | 5.5 | 5.0 | 5.5 | 6.7 |
| 24 hours before infection | 6.0 | 4.5 | 4.5 | 4.5 | 4.5 | 4.5 | 6.7 |
| 24 hours after infection | 0 | 2.8 | 0 | 0 | 1.8 | 0 | 6.7 |

It was shown that in the early period after the treatment of FEC cells with glutaryl histamine, the most pronounced antiviral properties of the drug was observed when it was added to FEC cultures 24 hours after infection. The study of samples of the culture fluid derived 48 hours after infection of the cells showed that under these conditions glutaryl histamine completely suppressed the infectious activity of HCV in the FEC cultures. In that period of time, the HCV titers in control untreated FEC cells reached 6.5 lg $TCID_{50}/20$ µl. Introduction of glutaryl histamine immediately after injection also decreased the HCV titers by 1.0-1.5 lg. When the cells were treated with glutaryl histamine 24 hours before infection, the HCV titers decreased by 2.0 lg.

SPEV (pig embryonic kidney cell) cultures were infected with a cytopathogenic HCV variant—C-13, and treated with various 10-fold dilutions of glutaryl histamine 24 hours before, immediately and 24 hours after infection. Samples of the culture medium were taken on Day 3, Day 4 and Day 5 after infection and titrated in fresh SPEV cell cultures.

The obtained results are shown in Tables 2-4. The data in the tables show that glutaryl histamine significantly suppresses the HCV replication in SPEV cell cultures when added to the cultures 24 hours after infection, similarly to FEC cells infected with HCV. These results remain stable regardless of the time of collection of fluid samples from the SPEV cell cultures treated with the drug. The ability of glutaryl histamine to suppress the HCV infectious activity by 2.2-2.7 lg $TCID_{50}/20$ µg was detected on Day 5 after infection and simultaneous treatment of the cells with the drug. The samples of medium collected on Day 5 after infection demonstrated that glutaryl histamine significantly suppressed the production of HCV, compared with the control: by 2.2 lg $TCID_{50}/20$ µg.

Thus, glutaryl histamine has an ability to suppress the replication of hepatitis C virus in infected 9-day chick embryo cultures, resulting to a significant decrease in titers of virus infectious activity. It has been shown that antiviral efficacy of glutaryl histamine is not decreased when HCV-infected cultures of another origin are used—SPEV-HCV cell lines. An effective suppression of an HCV infection has been shown in the model of infected SPEV-HCV cell cultures when glutaryl histamine was added to the cultures not only 24 hours after, but also 24 hours before infection. The obtained results evidence that glutaryl histamine has a significant antiviral activity against hepatitis C virus.

EXAMPLE 2

The study was aimed to determine clinic and laboratory efficacy of glutaryl histamine in patients with viral hepatitis C in a combined antiviral therapy (AVT) with pegylated interferons together with ribavirin.

Criteria of patient inclusion were the following: 1) the presence in patients of symptoms of an HCV infection—detection of anti-HVC antibodies by enzyme immunoassay (EIA); the presence of HCV RNA, 1b genotype, in blood serum (qualitative test); 2) a leukocyte level in a general blood test of from 3.9 to $3.0 \times 10^9$/L, a neutrophil level of from 2.0 to $1.5 \times 10^9$/L; 3) the absence of hepatitis B surface antigen; 4) the absence of human immunodeficiency virus antibodies; 5) the absence of other clinically significant liver diseases (alcoholic liver disease, administration of hepatotoxic pharmaceutical preparations, autoimmune chronic hepatitis, hemochromatosis); and 6) the absence of liver cirrhosis.

The patients were subcutaneously administered peg-interferon-α2b in a dose of 100 µg (or 1.5 µg/kg) once weekly and ribavirin in a dose of 1000 mg per day every day for 48 weeks. During the treatment patients were subjected to clinical and biochemical assessment. HCV RNA was determined one month after the therapy initiation and then every three months during the treatment. All patients were subjected to ultrasonic trans-abdominal scanning of the abdominal cavity organs before the treatment initiation and then every six months. The conducted study was approved by the Ethics Committee, and all patients gave informed consent to participate in the research study.

According to randomization (performed by an envelope method), all patients were divided into three groups comparable to sex and age, depending on the treatment scheme: Group 1 (n=52) was administered peg-interferon-α2b+ribavirin; and Group 2 (n=58) was administered peg-interferon-α2b+ribavirin+Dicarbamine (100 mg once daily), for 21 day from the treatment initiation. Further, Dicarbamine was administered according to similar scheme, every three months during the therapy.

Statistical analysis and graphic representation of data was performed according to modern computer-assisted analysis methods on an IBM-compatible computer with Microsoft Excel application of Office 2007 and Statistica (StatSoft) v.6 running under Microsoft Windows 7 Professional operating system.

Results and discussion The total amount of patients under observation was 110, in particular 69 (63%) mails and 41 (37%) females with hepatitis C, at the age of 19 to 52 years (an average age of 32.2±5.1 years). An average body weight was 76.4±8.1 (from 55 to 84 kg). The infection age, which was determined from the time of the manifestation of at least one risk factor, was from 2.5 to 8 years (Table 5). Reliable intergroup differences were not registered.

TABLE 5

Characteristic of the patients under observation (M ± m)

| Parameters | Group 1 | Group 2 |
|---|---|---|
| Number of patients | 52 | 58 |
| Males (persons) | 34 | 35 |
| Female (persons | 18 | 23 |
| Average age | 30.1 ± 4.2 | 31.4 ± 3.1 |
| Body weight, kg | 73.4 ± 3.2 | 72.8 ± 2.9 |
| Disease age, years | 4.5 ± 1.7 | 3.9 ± 2.2 |
| Initial ALT activity, U/L | 115.21 ± 7.24 | 112.41 ± 8.04 |
| Initial activity of alkaline phosphatase (ALP), U/L | 247.24 ± 12.5 | 257.34 ± 16.3 |
| Thymol test (TT), U | 5.8 ± 0.9 | 6.1 ± 1.1 |
| General level of bilirubin, μmol/L | 23.94 ± 0.82 | 24.01 ± 0.71 |
| Albumin, % | 51.98 ± 0.87 | 52.01 ± 0.74 |
| Gamma-globulins, % | 23.69 ± 0.71 | 23.45 ± 0.84 |
| Leukocyte level, $10^9$/L | 3.4 ± 0.08 | 3.3 ± 0.17 |
| Neutrophil level, $10^9$/L | 1.9 ± 0.11 | 1.8 ± 0.14 |

The basic syndromes in all patients with hepatitis C were asteno-vegetative syndrome (sleep disturbance, fatigue, hyperhydrosis, loss of appetite, mood swings) observed in 75 (67.95%) patients and dyspeptic syndrome (nausea, eructation, bursting feeling, heaviness in the epigastrium and right hypochondrium, constipation and/or diarrhea) observed in 62 (56.3%) patients. The most frequent clinical manifestation of the disease was hepatomegalia occurring in 94 (85.2%) patients. Splenomegaly occurred in 35 (31.95%) patients. The incidence of basic clinical syndromes in different groups of patients is shown in Table 6. The data in Table 6 show that before the therapy the two groups of patients had no significant differences.

TABLE 6

Incidence of clinical syndromes observed in patients before the therapy, %

| Symptoms | Group 1 | Group 2 | p |
|---|---|---|---|
| Dyspeptic syndrome | 54.2 | 58.4 | 0.701 |
| Asteno-vegetative syndrome | 66.2 | 69.7 | 0.839 |
| Hepatomegalia | 80.8 | 89.6 | 0.279 |
| Splenomegalia | 29.5 | 34.4 | 0.546 |
| Ochrodermia and scleral icterus | 14.5 | 20.2 | 0.622 |

Hyperenzymemia was registered in 38% patients and exceeded the normal level by 3 to 4 times, which corresponded to weak and moderate transaminase activity. In the rest of the patients, the ALT level was 1.5-2 times higher or did not exceed the normal level. Some patients had a slight hyperbilirubinemia with the bilirubin level increased twice of the normal value, preferably due to a non-conjugated fraction. Patients of the compared groups did not demonstrate significant differences. Dysproteinemia with hypergammaglobulinemia was observed in 34-36% of patients.

The groups of patients under observation were homogeneous by sex, age, nutritional conditions, living conditions and work activities, as well as place of residence.

Unlike the patients of Group 2, the patients of Group 1 tolerated the treatment worse, and side effects were detected more frequently. Data are shown in Table 7.

TABLE 7

Incidence of side-effects of the antiviral therapy, %

| Side effects | Group 1 | Group 2 | p |
|---|---|---|---|
| Influenza-like syndrome | 72.4 | 50.3 | 0.019 |
| Arthralgia | 62.1 | 44.6 | 0.089 |
| Myalgia | 58.3 | 32.4 | 0.012 |
| Exacerbation of chronic pancreatitis | 6.2 | 3 | 0.666 |
| Depression | 36.1 | 12.4 | 0.003 |
| Loss of hair | 38.4 | 14.1 | 0.004 |
| Cytopenic syndrome | 63.8 | 25.9 | 0.045 |
| Weight loss | 44.8 | 34.8 | 0.332 |

The percentage of registered side effects such as influenza-like syndrome, incidences of myalgia, depression, loss of hair and cytopenic syndrome, was lower than in patients of Group 1 ($p<0.05$).

In addition, the observation showed that 62.2% of the patients received antiviral combined therapy+Dicarbamine reported subjective improvement in wellbeing (increased performance and disappearance of fatigue) compared with 15.4% in Group 1, $p<0.05$.

The following side effects expressed in a reduction in the total amounts of leukocytes and neutrophils were observed during the antiviral therapy (Table 8). During AVT, 71% of patients of Group 1 had leukopenia and 69% of patients had neutropenia early in the treatment (4 weeks of the therapy), and these values were maintained at a significantly decreased level for the whole course of the treatment, compared with Group 2 ($p<0.05$). Leukopenia among the patients of Group 2 was detected in 35% cases, and neutropenia was observed in 46% of patients. In said group of patients there were not registered sharply decreased levels of leukocytes and neutrophils, which may cause adjustment of a dose or cessation of AVT.

TABLE 8

Hematological factors during the treatment period (M ± m)

| Parameters | | Group 1 | Group 2 |
|---|---|---|---|
| Leukocytes × $10^9$/L | Before the treatment | 3.4 ± 0.08 | 3.3 ± 0.17 |
| | 1 month after | 2.3 ± 0.12 | 3.1 ± 0.14* |
| | 2 months after | 2.4 ± 0.16 | 4.0 ± 0.18* |
| | 3 months after | 2.3 ± 0.11 | 3.8 ± 0.16* |
| | 6 months after | 2.7 ± 0.14 | 4.1 ± 0.21* |
| | 12 months after | 3.0 ± 0.10 | 3.7 ± 0.18* |
| Neutrophils × $10^9$/L | Before the treatment | 1.9 ± 0.11 | 1.8 ± 0.14 |
| | 1 month after | 1.2 ± 0.08 | 2.0 ± 0.07* |
| | 2 months after | 1.1 ± 0.06 | 2.3 ± 0.05* |

TABLE 8-continued

Hematological factors during the treatment period (M ± m)

| Parameters | Group 1 | Group 2 |
|---|---|---|
| 3 months after | 1.0 ± 0.05 | 2.0 ± 0.04* |
| 6 months after | 1.2 ± 0.06 | 2.3 ± 0.05* |
| 12 months after | 1.5 ± 0.04 | 2.1 ± 0.06* |

Note:
herein and further *validity of differences between parameters of Group 1 and Group 2 is p < 0.5.

An effect of Dicarbamine on biochemical parameters and a virological response was studied by assessing the efficacy of the administration thereof in complex therapy of patients with chronic hepatitis C (CHC). The most significant data are shown in Tables 9 and 10.

TABLE 9

Parameters of liver metabolism in the treatment of patients with chronic HCV infection (M ± m)

| Parameters | | Group 1 | Group 2 |
|---|---|---|---|
| ALT, U/L | 1 month after | 68.24 ± 4.37 | 49.21 ± 3.78* |
| | 3 months after | 89.47 ± 5.34 | 56.21 ± 4.34* |
| | 6 months after | 64.73 ± 5.43 | 50.38.4778* |
| | 12 months after | 49.34 ± 4.38 | 41.34 ± 3.52* |
| ALP, U/L | 1 month after | 221.41 ± 10.21 | 200.04 ± 12.43* |
| | 3 months after | 205.24 ± 8.73 | 161.02 ± 5.02* |
| | 6 months after | 197.36 ± 5.64 | 154.23 ± 4.73* |
| | 12 months after | 195.48 ± 4.03 | 155.03 ± 3.72 |
| TT, U | 1 month after | 5.03 ± 0.01 | 4.24 ± 0.41* |
| | 3 months after | 4.94 ± 0.03 | 3.84 ± 0.04* |
| | 6 months after | 4.79 ± 0.09 | 3.90 ± 0.03* |
| | 12 months after | 5.04 ± 0.08 | 4.03 ± 0.02* |
| Bilirubin, μmol/L | 1 month after | 22.48 ± 0.94 | 18.47 ± 0.08* |
| | 3 months after | 21.79 ± 0.74 | 16.24 ± 0.17 |
| | 6 months after | 20.73 ± 0.54 | 17.13 ± 0.21 |
| | 12 months after | 21.36 ± 0.98 | 17.04 ± 0.09* |
| Albumin, % | 1 month after | 52.04 ± 1.19 | 54.09 ± 1.23 |
| | 3 months after | 53.74 ± 1.41 | 55.47 ± 1.62 |
| | 6 months after | 55.03 ± 2.38 | 56.43 ± 2.05 |
| | 12 months after | 54.16 ± 1.17 | 55.36 ± 1.64 |
| γ-globulin, % | 1 month after | 23.47 ± 0.84 | 21.02 ± 0.34* |
| | 3 months after | 22.98 ± 0.97 | 19.91 ± 0.23* |
| | 6 months after | 23.04 ± 0.88 | 20.01 ± 0.31* |
| | 12 months after | 22.76 ± 0.11 | 21.32 ± 0.08* |

The data in Table 9 show that patients of Group 2 had more pronounced improvement in the parameters of cytolysis and cholestasis.

An immediate virological response (decrease in the HCV RNA level down to an indefinite level) was observed in 79.3% of patients of Group 2 additionally received Dicarbamine, which was statistically significant compared with the results for patients of Group 1 (p=0.035) received only combined antiviral therapy. These data are provided in Table 10. As can be seen from Table 10, the patients of Group 2 also had a statistically significant early virologic response more frequently (p<0.05).

TABLE 10

Efficacy of antiviral therapy, %

| Response variant | Group 1 | Group 2 | p |
|---|---|---|---|
| Rapid virologic response | 82.9 | 89.7 | 0.405 |
| Early virologic response | 65.9 | 86.2 | 0.013 |
| Immediate virologic response | 60.3 | 79.3 | 0.035 |

Thus, combined therapy of patients with viral hepatitis C, including peg-interferon, ribavirin and glutaryl histamine (as a constituent of Dicarbamine), is more effective for the treatment of hepatitis C. It has been noted that the patients with viral hepatitis C well tolerate the antiviral therapy according to the proposed scheme.

EXAMPLE 3

The study was aimed to determine an effect of glutaryl histamine (Dicarbamine) on the efficacy of antiviral therapy in patients with a chronic 1b genotype hepatitis C virus infection, which levels of leukocytes and neutrophils were initially decreased.

86 patients with CHC (anti-HCV "+", HCV RNA "+", genotype 1b) at the age of from 20 to 52 years (average age of 32±1.2 years) were under observation. Among them, 46 (53.5%) patients were male and 40 (46.5%) were female.

To achieve the aforesaid purpose, all patients were divided into two groups comparable to sex and age, depending on the treatment scheme: Group 1 (n=44) were administered peg-interferon-α2b+ribavirin; and Group 2 (n=42) received peg-interferon-α2b+ribavirin+Dicarbamine. Peg-interferon-α2b was administered subcutaneously in a dose of 100 μg (or 1.5 μg/kg) once weekly, and ribavirin in a dose of 1000 mg per day every day for 48 weeks. According to randomization (performed by an envelope method), Dicarbamine was administered in a dose of 100 mg once daily for 9 weeks from the antiviral therapy initiation and further 9 weeks before the treatment completion.

The treatment efficacy was assessed according to a sustained virologic response on the $24^{th}$ observation week after the treatment completion. The blood levels of leukocytes and neutrophils were measured before the treatment and at the control points of AVT (weeks 4, 8, 12, 24, 36, and 48). Reliable intergroup difference was not registered. Before the initiation of double AVT, all patients had laboratory symptoms of leuko- and neutropenia (the level of leukocytes in a general blood test was from 3.5 to $3.0 \times 10^9$/L, the level of neutrophils was from 2.0 to $1.5 \times 10^9$/L). The study was approved by the Ethics Committee, and all patients gave informed consent to participate in the research study.

Statistical analysis and graphic representation of data was performed according to modern computer-assisted analysis methods on an IBM-compatible computer with Microsoft Excel application of Office 2007 and Statistica (StatSoft) v.6 running under Microsoft Windows 7 Professional operating system.

Table 11 shows characteristics of the observed different group patients with CHC before the AVT initiation.

TABLE 11

Characteristic of the patients under observation (M ± m)

| Parameters | Group 1 | Group 2 |
|---|---|---|
| Number of patients | 44 | 42 |
| Males (persons) | 22 | 24 |
| Female (persons) | 22 | 18 |
| Average age | 31.1 ± 2.02 | 32.4 ± 2.01 |
| Body weight, kg | 70.4 ± 1.2 | 69.8 ± 2.9 |
| Disease age, years | 6.8 ± 1.7 | 7.1 ± 1.1 |
| Initial ALT activity, U/L | 125.21 ± 7.11 | 122.13 ± 8.15 |
| Initial ALP, U/L | 267.44 ± 14.6 | 271.34 ± 15.2 |
| TT, U | 6.8 ± 0.9 | 6.9 ± 1.1 |
| General level of bilirubin, μmol/L | 23.81 ± 1.81 | 24.04 ± 1.78 |
| Albumin, % | 52.23 ± 0.51 | 52.01 ± 0.54 |
| Gamma-globulins, % | 24.22 ± 0.41 | 24.78 ± 0.39 |
| Leukocyte level, $10^9$/L | 3.1 ± 0.16 | 3.2 ± 0.12 |
| Neutrophil level, $10^9$/L | 1.8 ± 0.13 | 1.7 ± 0.12 |
| HCV RNA level | $3.8 \times 10^6$ | $3.7 \times 10^6$ |

All patients with CHC had the following detected syndromes: 98% of patients had asteno-vegetative syndrome (increased fatigue, erethistic, sleep disturbance, decreased performance, general weakness, queasy, mood swings, headache), 90.9% of patients had dyspeptic syndrome (loss of appetite, abdominal discomfort, nausea, meteorism, eructation, and vomiting in some patients), 81% of patients had heaviness and/or pain in the epigastrium and/or the right hypochondrium (right hypochondrium syndrome) of predominantly aching and dull nature. Hepatomegalia was detected in 81% of the patients of this group, wherein large liver mass was accompanied with hardness in its consistency and moderate palpatory tenderness. In most patients (88.2%), these basic syndromes were observed simultaneously. The incidence of basic clinic syndromes in different groups of patients is shown in Table 12. Before the therapy initiation, significant differences between patients of Group 1 and Group 2 were not registered.

TABLE 12

Incidence of clinical syndromes observed in patients before the therapy, %

| Symptoms | Group 1 | Group 2 | p |
|---|---|---|---|
| Asteno-vegetative syndrome | 75.6 | 76.2 | 0.852 |
| Dyspeptic syndrome | 58.8 | 57.9 | 0.720 |
| Hepatomegalia | 86.8 | 88.1 | 0.226 |
| Splenomegalia | 34.4 | 35.1 | 0.525 |
| Right hypochondrium syndrome | 92.8 | 93.4 | 0.651 |

Analysis of blood dynamics of leukocytes and neutrophils in patients with CHC in the course of AVT, regardless of the treatment scheme, revealed that the percentage of patients with grade 1 leuko- and neutropenia was 83.7% before the treatment. As the AVT continued, the number of patients with reduced levels of leukocytes and neutrophils increased depending on the selected treatment scheme. Table 13 shows dynamics of absolute values of leukocytes and neutrophils in patients depending on the treatment scheme. Comparison of different variants of therapy showed that the use of peg-interferon in combination with ribavirin caused a significantly more pronounced decrease in the test parameters compared with the group of patients administered ribavirin. Thus, in Group 1 the minimum level of leukocytes was $2.1 \pm 0.16 \times 10^9/L$ and the minimum level of neutrophils was $1.0 \pm 0.03 \times 10^9/L$, whereas in Group 2 the minimum levels of leukocytes and neutrophils were $3.4 \pm 0.11 \times 10^9/L$ and $1.9 \pm 0.05 \times 10^9/L$, respectively (p<0.05).

TABLE 13

Dynamics of absolute values of leukocytes and neutrophils in patients with CHC, depending on the treatment scheme (M ± m)

| | Parameters | Group 1 peg-INF-α + ribavirin | Group 2 peg-INF-α + ribavirin + Dicarbamine |
|---|---|---|---|
| Leukocytes, $10^9/L$ | Before the treatment | 3.1 ± 0.16 | 3.2 ± 0.12 |
| | 4 weeks after the therapy | 2.2 ± 0.14 | 3.4 ± 0.11* |
| | 8 weeks after the therapy | 2.1 ± 0.16 | 3.8 ± 0.17* |
| | 12 weeks after the therapy | 2.2 ± 0.15 | 3.7 ± 0.16* |
| | 24 weeks after the therapy | 2.1 ± 0.18 | 4.0 ± 0.19* |
| | 36 weeks after the therapy | 2.8 ± 0.09 | 3.9 ± 0.18* |
| | 48 weeks after the therapy | 3.1 ± 0.11 | 3.7 ± 0.15* |
| | 24 weeks after the conducted AVT therapy | 3.5 ± 1.51 | 4.8 ± 1.38* |
| Neutrophils, $10^9/L$ | Before the treatment | 1.8 ± 0.13 | 1.7 ± 0.12 |
| | 4 weeks after the therapy | 1.1 ± 0.09 | 1.9 ± 0.05* |
| | 8 weeks after the therapy | 1.0 ± 0.03 | 2.1 ± 0.07* |
| | 12 weeks after the therapy | 1.1 ± 0.04 | 2.2 ± 0.05* |
| | 24 weeks after the therapy | 1.2 ± 0.08 | 2.2 ± 0.03* |
| | 36 weeks after the therapy | 1.4 ± 0.06 | 2.3 ± 0.08* |
| | 48 weeks after the therapy | 1.5 ± 0.04 | 2.2 ± 0.02* |
| | 24 weeks after the conducted AVT therapy | 2.4 ± 1.25 | 2.9 ± 1.18* |

Note:
*validity of differences between factors of Group 1 and Group 2 is p < 0.05

The conducted analysis of data on the efficacy of antiviral therapy showed that the best results of the treatment were obtained in Group 2 compared with Group 1 (p<0.05). The data are provided in Table 14.

TABLE 14

Efficacy of antiviral therapy, %

| Response variant | Group 1 | Group 2 | p |
|---|---|---|---|
| Rapid virologic response | 80.7 | 88.5 | 0.405 |
| Early virologic response | 66.2 | 85.8 | 0.013 |
| Immediate virologic response | 61.1 | 73.7 | 0.035 |
| Sustained virologic response | 44.8 | 65.5 | 0.028 |

Thus, it can be assumed that an antiviral effect can be potentiated by Dicarbamine when combined with AVT. Assay of long-term results of the conducted therapy revealed this property of Dicarbamine, namely a sustained virologic response.

Characteristics of the basic biochemical parameters in the two groups of patients with CHC were also compared before the AVT and 24 weeks after the AVT completion. The most significant data are shown in Table 15.

TABLE 15

Parameters of liver metabolism of patients with CHC before the treatment and 24 weeks after the AVT completion (M ± m)

| | Group 1 | | Group 2 | |
|---|---|---|---|---|
| Parameters | Before the AVT | 24 weeks after the AVT | Before the AVT | 24 weeks after the AVT |
| ALT, U/L | 125.21 ± 7.11 | 56.85 ± 8.56 | 122.13 ± 8.15 | 39.42 ± 6.39* |
| ALP, U/L | 267.44 ± 14.6 | 228 ± 17.11 | 271.34 ± 15.2 | 169 ± 12.45* |
| TT, U | 6.8 ± 0.9 | 6.6 ± 0.81 | 6.9 ± 1.1 | 5.8 ± 0.92 |

TABLE 15-continued

Parameters of liver metabolism of patients with CHC before the treatment and 24 weeks after the AVT completion (M ± m)

| Parameters | Group 1 | | Group 2 | |
|---|---|---|---|---|
| | Before the AVT | 24 weeks after the AVT | Before the AVT | 24 weeks after the AVT |
| Albumin, % | 52.23 ± 0.51 | 51.23 ± 0.11 | 52.01 ± 0.54 | 54 ± 0.26* |
| γ-globulin, % | 24.22 ± 0.41 | 23.67 ± 0.51 | 24.78 ± 0.39 | 20.56 ± 0.42 |

Note:
*validity of differences between factors of Group 1 and Group 2 is p < 0.05

Data in Table 15 show that the parameters of cytolysis and cholestasis were significantly improved in patients of Group 2 weeks after the conducted therapy. Administration of Dicarbamine to patients of Group 2 showed statistically significant long-term results on recovery of the parameter of liver metabolism.

Thus, the prescription of Dicarbamine in combination with double antiviral therapy is a new method for treating HCV infection.

Addition of Dicarbamine to combined antiviral therapy resulted in an increase in the rate of a sustained virologic response in patients with chronic hepatitis C (CHC), thus increasing the treatment efficacy by 20.7%.

EXAMPLE 4

The study was aimed to determine an effect of the treatment with Dicarbamine on the efficacy of antiviral therapy in primary patients with CHC to achieve a sustained virologic response.

142 patients (66 male and 76 female at the age of from 18 to 62 years, the average age of 36.5±1.4 years) were under observation. Patient inclusion criteria were the presence in patients of confirmed (by anamnestic and clinical laboratory data) CHC in the replication phase (HCV RNA +), viral genotypes 1b and 3a; the absence of human immunodeficiency virus antigens; the absence of other clinically significant liver diseases (alcoholic liver disease, administration of hepatotoxic pharmaceutical preparations, autoimmune chronic hepatitis, hemochromatosis); and the absence of liver cirrhosis. All patients were subjected to a complex observation by clinical laboratory assay methods. CHC diagnosis was supported by the revelation of specific antibodies to hepatitis C virus (anti-HCV IgG, total anti-HCV) antigens and HCV RNA by the polymerase chain reaction (PCR) method in the blood serum with determination of the genotype and amount of the virus. During the treatment, patients were subjected to monthly clinical and biochemical assessment. HCV RNA was examined one month after the therapy initiation and then every three months during the treatment. All patients were subjected to ultrasonic trans-abdominal scanning of the abdominal cavity organs before the treatment initiation, and then every six months. In addition, 56 apparently healthy persons with a body-weight index of less than 25 kg/m$^2$, without hepatitis C markers, which immune-biochemical parameters were normal, also were examined as a control group.

The body-weight index of all patients involved in the study was 18-25 kg/m$^2$. Genotype 1b was revealed in 54.9% of patients, the rest of patients (45.1%) had genotype 3a. The viral load varied from 240×10$^3$ to 12×10$^6$ IU/ml.

84 patients were subjected to liver punch biopsy to determine more precisely the degree of activity and state of the disease: the mean value of a histological activity index (HAI) according to Rnodell was 6.02±0.71 score, and a fibrosis index according to Desmet was 1.08±0.92 score.

The patients were received peg-interferon-α2b in a dose of 1.5 μg/kg/week and ribavirin (800-1200 mg/day) every day. Duration of treatment for genotype 3a with a rapid virologic response was 24 weeks, and for genotype 1b with an early virologic response was 48 weeks.

The conducted study was approved by the Ethics Committee, and all patients gave informed consent to participate in the research study.

According to randomization (performed by an envelope method), all patients were divided into three groups comparable to sex and age depending on the treatment scheme: the first group (n=74) was administered peg-interferon-α2b+ribavirin; and the second group (n=68) was administered peg-interferon-α2b+ribavirin+Dicarbamine (100 mg once weekly), for 12 weeks from the treatment initiation. Further, Dicarbamine was administered in the same dose for the last 12 weeks of the AVT.

Compared groups were comparable by sex, age, viral genotype, and biochemical parameters (Tables 16 and 17).

Statistical analysis and graphic representation of data was performed according to modern computer-assisted analysis methods on an IBM-compatible computer with Microsoft Excel application of Office 2007 and Statistica (StatSoft) v7.0 running under Microsoft Windows XP Professional operating system.

TABLE 16

Characteristic of the patients under observation (M ± m)

| | Healthy | Group 1 | Group 2 |
|---|---|---|---|
| The number of patients | 56 | 74 | 68 |
| Male | 26 | 35 | 31 |
| Female | 30 | 39 | 37 |
| Average age, years | 35.3 ± 1.1 | 35.2 ± 1.3 | 36.1 ± 1.4 |
| BMI, kg/m$^2$ | 21.2 ± 2.12 | 21.5 ± 2.09 | 21.1 ± 2.01 |
| HAI, score | — | 5.99 ± 0.82 | 6.01 ± 0.55 |
| Fibrosis index | — | 1.16 ± 0.71 | 1.11 ± 0.32 |
| Viral genotype 1b | — | 38 | 40 |
| Viral genotype 3a | — | 36 | 28 |
| Viral load <800,000 IU/ml | — | 29 | 23 |
| Viral load >800,000 IU/ml | — | 45 | 45 |

TABLE 17

Characteristic of the patients under observation according to biochemical parameters (M ± m)

| Parameters | Healthy | Group 1 | Group 2 |
|---|---|---|---|
| Initial ALT activity, U/L | 22.74 ± 0.69 | 125.31 ± 5.19 | 126.84 ± 8.22 |
| Initial ALP activity, U/L | 119.59 ± 1.83 | 259.56 ± 7.13 | 237.11 ± 6.22 |
| TT, U | 2.11 ± 0.06 | 2.69 ± 0.14 | 3.59 ± 0.11 |
| General bilirubin, μmol/L | 17.13 ± 0.28 | 24.51 ± 0.69 | 26.04 ± 0.61 |
| Albumins, % | 62.44 ± 0.36 | 51.81 ± 0.69 | 53.24 ± 0.59 |
| γ-globulin, % | 18.07 ± 0.15 | 22.58 ± 0.40 | 21.57 ± 0.31 |

Concomitant therapy with Dicarbamine was tolerable for all patients. The incidence of adverse effects in patients of Group 2 was determined by side effects caused by peg-interferon and ribavirin. The assessment of the blood levels of leukocytes and neutrophils in patients with CHC during the AVT, depending the treatment scheme, is provided in Table 18.

TABLE 18

Hematological factors during the treatment (M ± m)

| | Parameters | Group 1 | Group 2 |
|---|---|---|---|
| Leukocytes, $10^9$/L | Before the treatment | 5.4 ± 0.08 | 5.3 ± 0.17 |
| | 1 month after the therapy | 2.3 ± 0.12 | 3.1 ± 0.14* |
| | 2 months after the therapy | 2.4 ± 0.16 | 4.0 ± 0.18* |
| | 3 months after the therapy | 2.3 ± 0.11 | 3.8 ± 0.16* |
| | 6 months after the therapy | 2.7 ± 0.14 | 4.1 ± 0.21* |
| | 12 months after the therapy | 3.0 ± 0.10 | 3.7 ± 0.18* |
| Neutrophils, $10^9$/L | Before the treatment | 2.9 ± 0.11 | 2.8 ± 0.14 |
| | 1 month after the therapy | 1.2 ± 0.08 | 2.0 ± 0.07* |
| | 2 months after the therapy | 1.1 ± 0.06 | 2.3 ± 0.05* |
| | 3 months after the therapy | 1.0 ± 0.05 | 2.0 ± 0.04* |
| | 6 months after the therapy | 1.2 ± 0.06 | 2.3 ± 0.05* |
| | 12 months after the therapy | 1.5 ± 0.04 | 2.1 ± 0.06* |

Note:
herein and further: *validity of differences between factors of Group 1 and Group 2 is $p<0.5$ It was noted that absolute blood parameters (leukocytes and neutrophils) statistically significantly decreased in the patients of two groups in Week 4 of the treatment. However, a decrease in these parameters registered in Group 2 was less pronounced than in Group 1 in all control test points ($p<0.05$).

Analysis of biochemical parameters demonstrated that results in patients of Group 2 were statistically significantly better then in Group 1. The results are given in Table 19.

TABLE 19

Characteristic of the patients under observation according to biochemical parameters 6 months after the treatment completion (M ± m)

| Parameters | Healthy | Group 1 | Group 2 |
|---|---|---|---|
| ALT, U/L | 22.74 ± 0.69 | 118.32 ± 5.88<br>$p_0 < 0.001$<br>$p_{1-2} < 0.001$ | 21.89 ± 1.45<br>$p_0 = 1.000$ |
| ALP, U/L | 119.59 ± 1.83 | 261.63 ± 6.99<br>$p_0 < 0.001$<br>$p_{1-2} < 0.001$ | 160.24 ± 4.83<br>$p_0 < 0.001$ |
| TT, U | 2.11 ± 0.06 | 6.11 ± 0.21<br>$p_0 < 0.001$<br>$p_{1-2} < 0.001$ | 4.69 ± 0.19<br>$p_0 < 0.01$ |

Notes:
Herein and further: p - probability of incorrectly accepting alternative hypothesis suggesting the presence of intergroup differences, $p_0$ is probability of incorrectly accepting alternative hypothesis suggesting differences with parameters of a control group (health), and $p_{1-2}$ is probability of incorrectly accepting alternative hypothesis suggesting differences between parameters of patients of Group 1 and Group 2

Data in Table 19 showed that in patients of Group 1, apparent cytolysis syndrome was steady. The ALT level increased from 30.4 to 183.2 U/L and exceeded the normal level in 36% of patients. The mean value of this parameter was 118.32±5.88 U/L, which was statistically significantly ($p_0<0.001$, $p_{1-2}<0.001$) different from similar parameters in the comparison groups. The mean ALT value in patients of Group 2 was 21.89±1.45 U/L and did not exceed the normal values in 88% of patients. The values of ALP and TT in patients of Group 1 and Group 2 also were statistically significantly different from each other and from the group of healthy persons (Table 19). It was noted that thymol test and the ALP values in patients of Group 1 were increased, 86.4% and 65.5%, respectively.

The main result of this study is presented by differences in the rate of achieving rapid, early and sustained virologic responses depending on a viral genotype (Tables 20 and 21).

TABLE 20

Virologic response rate for hepatitis C virus genotype 1b in various treatment schemes

| | Genotype | | |
|---|---|---|---|
| Response type | Group 1<br>1b | Group 2<br>1b | p |
| Rapid virologic response | 52.63% | 75% | $p < 0.05$ |
| Early virologic response | 78.95% | 82.5% | $p > 0.05$ |
| Immediate virologic response | 71.05% | 82.5% | $p < 0.05$ |
| Sustained virologic response | 47.37% | 67.5% | $p < 0.05$ |

TABLE 21

Virologic response rate for hepatitis C virus genotype 3a in various treatment schemes

| | Genotype | | |
|---|---|---|---|
| Response type | Group 1<br>3a | Group 2<br>3a | p |
| Rapid virologic response | 83.33% | 98.93% | $p < 0.05$ |
| Early virologic response | 76.89% | 99.14% | $p < 0.05$ |
| Immediate virologic response | 74.33% | 86.86% | $p > 0.05$ |
| Sustained virologic response | 71.33% | 89.29% | $p < 0.05$ |

Administration of Dicarbamine was accompanied by higher rate of achieving all types of a virologic response. Thus, the rate of achieving a rapid virologic response (RVR, in 4 weeks of the AVT) in patients of Group 2 for genotype 1b was 75%, and for genotype 3a was 98.93% compared with 52.63% and 83.33% in the group without its administration. The rate of achieving an early virologic response (EVR, in 12 weeks of the AVT) and a sustained virologic response (SVR, in 6 months after the treatment completion) also were higher in the group of patients administered Dicarbamine: RVR, EVR and SVR for genotype 1b were 82.5%, 82.5% and 67.5%, and for genotype 3a were 99.14%, 86.86%, and 89.29%, compared to 78.95%, 71.05%, 47.37% and 76.89%, 74.33%, 71.33%, respectively.

Unlike patients of Group 1, the patients of Group 2 tolerated the treatment better, and side effects were detected more rarely. Patient observation data are shown in Table 22.

TABLE 22

| Side effects | Group 1 | Group 2 | p |
|---|---|---|---|
| Influenza-like syndrome | 78.38 | 51.47 | 0.001 |
| Arthralgia | 63.51 | 44.12 | 0.028 |
| Myalgia | 58.11 | 32.35 | 0.003 |
| Exacerbation of chronic pancreatitis | 6.76 | 32.94 | 0.444 |
| Depression | 36.49 | 11.76 | 0.001 |
| Loss of hair | 37.84 | 13.24 | 0.001 |
| Cytopenic syndrome | 63.51 | 25 | 0.000 |
| Weight loss | 44.59 | 33.82 | 0.230 |

Thus, Dicarbamine can be considered as a preparation enhancing an antiviral action simultaneously with administration of peg-interferon and ribavirin, which is evident in an increase in a SVR rate for genotype 1b by 20.13%, and for genotype 3a by 17.96%.

Thus, it has been found that the treatment of CHC patients with pegylated interferon-α2b+ribavirin in combination with Dicarbamine has a positive effect on biochemical parameters in patients, which are evident in an improvement of functional activity of hepatocytes. In addition, the use of Dicarbamine in the treatment of CHC is associated with reliably higher rate of achieving SVR in the course of AVT in patients having genotypes 1b and 3a. In addition, the treatment with Dicarbamine (genotypes 1b and 3a) is accompanied with statistically significant decrease of the rate of adverse effects of AVT.

EXAMPLE 5

Dosage Forms of Glutaryl Histamine

For the treatment of hepatitis C, glutaryl histamine can be administered orally, intramuscularly or intravenously in unit dosage forms comprising non-toxic pharmaceutically acceptable carriers.

Glutaryl histamine may be administered to a patient in doses of from 0.1 to 10 mg/kg of body weight, preferably in doses of from 0.5 to 5 mg/kg, more preferably 1 mg/kg, one or more times a day.

In addition, it must be noted that a particular dose for a particular patient will depend on many factors, such as patient's age, body weight, sex, general health condition, and dietary, and the schedule and route of administration of a drug and its excretion rate from the body, as well as the disease severity in the patient under treatment.

Pharmaceutical compositions comprise glutaryl histamine in an amount effective for providing a desired result in the treatment of hepatitis C, and may be administered in unit dosage forms (for example, in solid, semi-solid, or liquid forms) that comprise glutaryl histamine as an active agent in combination with a carrier or an excipient suitable for oral, intramuscular or intravenous administration. The active ingredient may be in the composition together with conventional nontoxic, pharmaceutically acceptable carriers suitable for manufacturing solutions, tablets, pills, capsules, pellets, and any other dosage forms.

Various compounds may be used as excipients, for example, such as saccharides, for example, glucose, lactose, or sucrose; mannitol or sorbitol; cellulose derivatives; and/or calcium phosphates, for example, tricalcium phosphate or acid calcium hydrophosphate. As binders there can be used starch paste (for example, corn, wheat, rice, or potato starch), gelatin, tragacanth, methylcellulose, hydroxypropyl methylcellulose, sodium carboxymethyl cellulose, and/or polyvinylpyrrolidone. If necessary, disintegrating agents, such as the aforementioned starches and carboxymethyl starch, crosslinked polyvinylpyrrolidone, agar-agar, or alginic acid or a salt thereof, such as sodium alginate, may be used.

Optional additives, for example, flowability control agents and lubricating agents, such as silica, talc, stearic acid and salts thereof, such as magnesium stearate or calcium stearate, and/or propylene glycol, also may be added.

A stabilizing agent, a thickening agent, colorant, and fragrance may be also used as additives.

In a unit dosage form, the amount of an active agent used in combination with a carrier may vary depending on a patient under the therapy and on the route of administration of the therapeutic agent.

For example, when glutaryl histamine is used in the form of solutions for injection, the active agent in this solution is in an amount of 0.01 to 5 wt. %. As diluents, 0.9% sodium chloride solution, distilled water, Novocaine solution for injections, Ringer solution, glucose solution, and specific solubilizing adjuvants may be used. When glutaryl histamine is administered in the form of tablets, its amount ranges 5.0 to 500 mg per unit dosage form.

Dosage forms of glutaryl histamine used according to the present invention are prepared by standard methods such as, for example, processes of mixing, granulation, forming pills, dissolution and lyophilization.

Tableted Form

Tableted form is prepared by using the following ingredients:

| | |
|---|---|
| Glutaryl histamine or a pharmaceutically acceptable salt thereof | 1-100 mg |
| Potato starch | 20-50 mg |
| Magnesium stearate | 3 mg |
| Aerosil | 1 mg |
| Lactose | up to 300 mg |

The ingredients are mixed and compressed to form tablets weighing 300 mg each.

Suppositories

Example of the formulation of a suppository

| | |
|---|---|
| Glutaryl histamine or a pharmaceutically acceptable salt thereof | 1-100 mg |
| Cacao oil | amount required for a suppository |

Rectal, vaginal, and urethral suppositories can be optionally prepared with corresponding excipients.

Solution for Injection

Example of the formulation of a solution for injections:

| | |
|---|---|
| Glutaryl histamine or a pharmaceutically acceptable salt thereof | 1-50 mg |
| Water for injection | 2 ml |

The invention claimed is:

1. An agent for the treatment of viral hepatitis C, comprising glutaryl histamine or a pharmaceutically acceptable salt thereof, pegylated interferon and ribavirin.

2. The agent according to claim 1, wherein the pegylated interferon is pegylated interferon-α2a.

3. The agent according to claim 1, wherein the pegylated interferon is pegylated interferon-α2b.

4. A pharmaceutical composition for the treatment of viral hepatitis C, comprising an effective amount of the agent of claim 1.

5. The pharmaceutical composition according to claim 4, wherein the effective amount of the glutaryl histamine or the pharmaceutically acceptable salt thereof is from 0.1 to 10 mg/kg of body weight.

6. The pharmaceutical composition according to claim 4, further comprising pegylated interferon and ribavirin.

7. The pharmaceutical composition according to claim 4, wherein the viral hepatitis C is acute hepatitis C.

8. The pharmaceutical composition according to claim 4, wherein the viral hepatitis C is chronic hepatitis C.

9. The pharmaceutical composition according to claim 4, wherein the glutaryl histamine is a constituent of a Dicarbamine preparation.

10. The pharmaceutical composition according to claim 6, wherein the pegylated interferon is pegylated interferon-α2a.

11. The pharmaceutical composition according to claim 6, wherein the pegylated interferon is pegylated interferon-α2b.

12. A kit for the treatment of viral hepatitis C, comprising pegylated interferon, ribavirin, glutaryl histamine or a pharmaceutically acceptable salt thereof, and the instructions for use.

13. A method for treating viral hepatitis C or achieving a sustained virologic response in the treatment of viral hepatitis C, comprising administering to a patient an effective amount of glutaryl histamine or a pharmaceutically acceptable salt thereof.

14. The method according to claim 13, wherein the viral hepatitis C is acute hepatitis C.

15. The method according to claim 13, wherein the viral hepatitis C is chronic hepatitis C.

16. The method according to claim 13, wherein the glutaryl histamine is administered as a constituent of a Dicarbamine preparation.

17. The method of according to claim 13, wherein a dose of the glutaryl histamine or the pharmaceutically acceptable salt thereof is from 0.1 to 10 mg/kg of body weight.

18. The method of according to claim 13, wherein a single dose of the glutaryl histamine is 100 mg.

19. The method of according to claim 13, wherein a duration of administration of the glutaryl histamine is from 3 weeks to 12 months.

20. A method for treating viral hepatitis C, comprising administering to a patient an effective amount of glutaryl histamine or a pharmaceutically acceptable salt thereof, wherein the glutaryl histamine is administered as a constituent of a Dicarbamine preparation and the method further comprises administering pegylated interferon and ribavirin, wherein the treatment of hepatitis C provides a decrease in side effects of antiviral therapy, relative to treatment without administering glutaryl histamine.

21. The method according to claim 20, wherein the side effects of antiviral therapy are influenza-like syndrome, arthralgia, myalgia, exacerbation of chronic pancreatitis, depression, and/or loss of hair.

22. The method according to claim 20, wherein the side effects of antiviral therapy are leukopenia or neutropenia.

23. The method according to claim 13, further comprising administering to the patient pegylated interferon and ribavirin.

24. The method according to claim 23, wherein the pegylated interferon is pegylated interferon-α2a.

25. The method according to claim 23, wherein the pegylated interferon is pegylated interferon-α2b.

26. The method according to claim 23, wherein a dose of the pegylated interferon is 100 μg or 1.5 μg/kg when administered once weekly.

27. The method according to claim 23, wherein a dose of ribavirin is 1000 mg per day when administered once daily.

* * * * *